US008431002B2

(12) United States Patent
Wakazono et al.

(10) Patent No.: US 8,431,002 B2
(45) Date of Patent: Apr. 30, 2013

(54) GAS SENSOR

(75) Inventors: Tomohiro Wakazono, Konan (JP); Seiji Oya, Niwa-gun (JP)

(73) Assignee: NGK Spark Plug Co., Ltd., Aichi (JP)

( * ) Notice: Subject to any disclaimer, the term of this patent is extended or adjusted under 35 U.S.C. 154(b) by 329 days.

(21) Appl. No.: 12/732,780

(22) Filed: Mar. 26, 2010

(65) Prior Publication Data
US 2010/0243444 A1  Sep. 30, 2010

(30) Foreign Application Priority Data

Mar. 27, 2009  (JP) ................................. 2009-078169
Feb. 18, 2010  (JP) ................................. 2010-033137

(51) Int. Cl.
*G01N 27/417*  (2006.01)

(52) U.S. Cl.
USPC ......... 204/424; 204/410; 205/783.5; 205/784

(58) Field of Classification Search ............... 204/413, 204/431, 424–429; 422/98; 205/781, 783.5–785; 73/23.31, 23.32
See application file for complete search history.

(56) References Cited

U.S. PATENT DOCUMENTS 5,137,615 A * 8/1992 Friese et al. ................. 204/424
5,942,190 A * 8/1999 Kato et al. ................... 422/98
2004/0231985 A1 * 11/2004 Kato et al. ................... 204/426
2007/0000780 A1 * 1/2007 Oya et al. .................... 204/424

FOREIGN PATENT DOCUMENTS

JP  09-288085 A  11/1997

* cited by examiner

*Primary Examiner* — Alex Noguerola
*Assistant Examiner* — Steven Rosenwald
(74) *Attorney, Agent, or Firm* — Sughrue Mion, PLLC

(57) ABSTRACT

A gas sensor includes a gas sensor element. The gas sensor element includes a first detection chamber; a first oxygen pumping cell including a first solid electrolyte body and a pair of first electrodes; a second detection chamber; a second oxygen pumping cell including a second solid electrolyte body and a pair of second electrodes; and an oxygen-concentration sensing cell including a third solid electrolyte body and a pair of third electrodes. A sensing electrode of the third electrodes is disposed downstream beyond a first inner electrode of the first electrodes relative to a gas flow direction. A cross-sectional area of a space of the first detection chamber which faces the first inner electrode falls within a range from 0.03 mm$^2$ to 0.22 mm$^2$. A center of the sensing electrode is located downstream beyond a downstream end of the first inner electrode to cause a distance between the center of the sensing electrode and the downstream end of the first inner electrode to be greater than or equal to ten times magnitude of a height of the space.

9 Claims, 8 Drawing Sheets

GAS SENSOR

BACKGROUND OF THE INVENTION

The present invention relates to a gas sensor.

There has been a gas sensor adapted to detect a specific gas component such as nitrogen oxide (NOx) or oxygen, or adapted to measure a concentration of the specific gas component. As such a gas sensor, U.S. Pat. No. 5,942,190 corresponding to Japanese Patent Application Publication No. H9(1997)-288085 discloses a previously-proposed gas sensor. In this technique, an oxygen pumping cell for adjusting oxygen concentration within a detection chamber (gas chamber) is controlled by way of feedback control on the basis of signals derived from a cell (oxygen-concentration sensing cell) for detecting the oxygen concentration within the detection chamber.

SUMMARY OF THE INVENTION

A downsizing of the detection chamber produces various advantages. For example, an oxygen-pumping efficiency of the oxygen pumping cell can be enhanced. Thereby, a power consumption which is used for the pumping can be reduced. Moreover, a gas sensor element can be downsized. Accordingly, a temperature difference between different locations in the gas sensor element can be reduced. However, a gas amount (amount per unit time) which flows into the detection chamber is reduced due to the downsizing of detection chamber. Because of this reduction of gas amount, an amount of specific gas component to be detected by the gas sensor is also reduced, and thereby, there is a possibility that a detection accuracy of the specific gas component is lowered. Contrary to this, in order to enhance the detection accuracy of specific gas component, it is preferable that various errors affecting the detection accuracy are made smaller. Inventors of the present application have discovered that a reduction of detection error of the oxygen-concentration sensing cell is effective in enhancing the detection accuracy of specific gas component, particularly in the case that the detection chamber is downsized.

Therefore, it is an object of the present invention to provide a technique capable of achieving both of a downsizing of gas sensor and a favorable detection accuracy of the gas sensor.

According to one aspect of the present invention, there is provided a gas sensor comprising a gas sensor element, the gas sensor element comprising: a first detection chamber into which a gas to be detected is introduced through a first diffusion resisting portion; a first oxygen pumping cell including a first solid electrolyte body and a pair of first electrodes formed on the first solid electrolyte body, wherein the pair of first electrodes include a first inner electrode disposed within the first detection chamber, wherein the first oxygen pumping cell is configured to pump oxygen from/into the gas which has been introduced into the first detection chamber; a second detection chamber into which the gas given the oxygen pumping in the first detection chamber is introduced through a second diffusion resisting portion; a second oxygen pumping cell including a second solid electrolyte body and a pair of second electrodes formed on the second solid electrolyte body, wherein the pair of second electrodes include an inside second pumping electrode disposed within the second detection chamber, wherein the second oxygen pumping cell is configured to pass an electric current according to a concentration of specific gas component within the second detection chamber; and an oxygen-concentration sensing cell including a third solid electrolyte body and a pair of third electrodes disposed on the third solid electrolyte body, wherein the pair of third electrodes include a sensing electrode disposed within the first detection chamber, wherein the oxygen-concentration sensing cell is configured to generate a voltage between the third electrodes in accordance with an oxygen concentration within the first detection chamber; wherein the sensing electrode is disposed downstream beyond the first inner electrode relative to a flow direction of the gas, wherein a cross-sectional area of a space of the first detection chamber through which the gas flows falls within a range from 0.03 $mm^2$ to 0.22 $mm^2$, the space facing the first inner electrode, wherein a center of the sensing electrode is located downstream beyond a downstream end of the first inner electrode to cause a distance between the center of the sensing electrode and the downstream end of the first inner electrode to be greater than or equal to ten times magnitude of a height of the space, the height being a length taken in a laminating direction between the first solid electrolyte body and the first inner electrode.

The other objects and features of this invention will become understood from the following description with reference to the accompanying drawings.

DETAILED DESCRIPTION OF THE INVENTION

Reference will hereinafter be made to the drawings in order to facilitate a better understanding of the present invention. Embodiment and modified embodiments according to the present invention will be explained in the following sequence.

(A) Embodiment
(B) Modified Embodiments

(A) Embodiment

Figure 1:
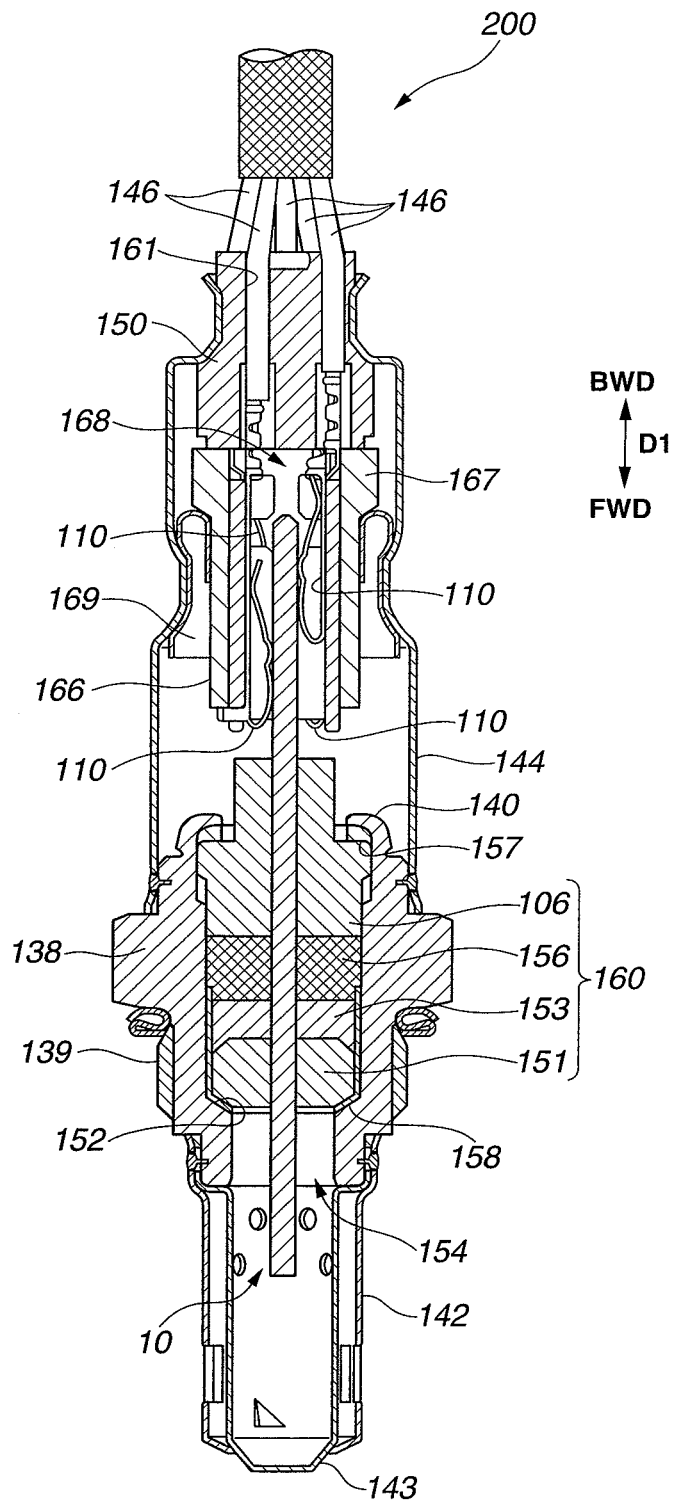
FIG. 1 is a cross-sectional view showing a gas sensor 200 in one embodiment according to the present invention.

FIG. 1 is a cross-sectional view showing a gas sensor 200 in one embodiment according to the present invention. The gas sensor 200 is fixed to an exhaust pipe of an internal combustion engine (not shown), and measures a concentration of nitrogen oxide(s) (NOx). Hereinafter, the gas sensor 200 will be also referred to as "NOx sensor 200". FIG. 1 shows a cross section of the NOx sensor 200, taken parallel to a longitudinal direction D1 of the NOx sensor 200. Hereinafter, a lower direction (lower side) in FIG. 1 is referred to as a frontward direction (front-end side) FWD of the NOx sensor 200, and an upper direction (upper side) in FIG. 1 is referred to as a backward direction (back-end side) BWD of the NOx sensor 200.

The NOx sensor 200 includes a mounting metal body 138 formed in a shape of cylindrical tube, a NOx sensor element (gas sensor element) 10 formed in a plate shape extending in the longitudinal direction D1, a ceramic sleeve 106 formed in a shape of cylindrical tube to surround the NOx sensor element 10, an insulating contact member 166, and six connecting terminals 110 (four connecting terminals 110 are shown in FIG. 1). An outer surface of the mounting metal body 138 is formed with a threaded portion 139 for being fixed to the exhaust pipe. The ceramic sleeve 106 is placed radially around the NOx sensor element 10, i.e., surrounds an outer circumference of the NOx sensor element 10. The insulating contact member 166 is formed with a contact insertion hole 168. The contact insertion hole 168 passes through the insulating contact member 166 in the longitudinal direction D1. The insulating contact member 166 is disposed to locate an inner wall surface of contact insertion hole 168 around a backward portion (back-end portion) of the NOx sensor element 10, i.e., is disposed to cause the inner wall surface of contact insertion hole 168 to surround an outer circumference of the backward portion of the NOx sensor element 10. The respective connecting terminals 110 are disposed between the NOx sensor element 10 and the insulating contact member 166.

The mounting metal body 138 is formed with a through-hole 154. The through-hole 154 passes through the mounting metal body 138 in an axial direction thereof. The mounting metal body 138 is formed substantially in a shape of cylindrical tube, and includes a stepped portion 152 protruding in a radially inner direction of the through-hole 154. The mounting metal body 138 holds the NOx sensor element 10 in the through-hole 154, so as to place a frontward end (front end) of the NOx sensor element 10 outside the through-hole 154 in the frontward direction (on FWD side), and to place a backward side of the NOx sensor element 10 outside the through-hole 154 in the backward direction (on BWD side). The stepped portion 152 has a conically tapered surface inclined from a plane perpendicular to the longitudinal direction D1. This tapered surface is formed to cause a diameter of frontward side (FWD-side portion) of the tapered surface to be smaller than a diameter of backward side (BWD-side portion) of the tapered surface.

Within the through-hole 154 of the mounting metal body 138, a ceramic holder 151, powder-filled layers 153 and 156 (hereinafter, also referred to as talc rings 153 and 156), and the ceramic sleeve 106 are arranged or laminated in this order from the frontward side toward the backward side of through-hole 154. Whole of the ceramic holder 151, the talc rings 153 and 156 and the ceramic sleeve 106 defines a holding portion for holding the NOx sensor element 10, and is hereinafter also referred to as "holding portion 160". This holding portion 160, namely, each of the ceramic holder 151, the talc rings 153 and 156 and the ceramic sleeve 106 is formed in an annular shape capable of radially surrounding the NOx sensor element 10, i.e., is formed in an annular shape surrounding (or fitting over) the outer circumference of the NOx sensor element 10. Thus, the NOx sensor element 10 is held by the holding portion 160.

A swage packing 157 is disposed between the ceramic sleeve 106 and a backward end portion 140 of the mounting metal body 138. A metal holder 158 for holding the talc ring 153 and the ceramic holder 151 and for maintaining an air tightness is disposed between the ceramic holder 151 and the stepped portion 152 of the mounting metal body 138. The backward end portion 140 of the mounting metal body 138 is swaged so as to press the ceramic sleeve 106 through the swage packing 157 in the frontward direction.

As shown in FIG. 1, an outer protector 142 and an inner protector 143 are attached to an outer circumference of frontward side of the mounting metal body 138 (a lower side of the mounting metal body 138 in FIG. 1) by welding or the like. Each of these two protectors 142 and 143 is formed of a metal such as stainless and includes a plurality of holes. These outer and inner protectors 142 and 143 cover a protruding portion of the NOx sensor element 10.

An outer tube 144 is fixed to an outer circumference of backward side of the mounting metal body 138. A grommet 150 is provided in an opening portion of backward side (upper side in FIG. 1) of the outer tube 144. The grommet 150 is formed with lead-wire insertion holes 161. Six lead wires 146 are inserted into the lead-wire insertion holes 161 (only five lead wires 146 are shown in FIG. 1). Respective lead wires 146 are electrically connected with electrode pads (not shown) provided to an outer surface of backward side of the NOx sensor element 10.

The insulating contact member 166 is provided at a backward end portion (upper side in FIG. 1) of NOx sensor element 10 which protrudes from the backward end portion 140 of the mounting metal body 138. In detail, this insulating contact member 166 is disposed around the electrode pads (not shown) formed at the outer surface of backward side of NOx sensor element 10. The insulating contact member 166 is formed in a shape of cylindrical tube having the contact insertion hole 168 passing through the insulating contact member 166 in the longitudinal direction D1. Moreover, the insulating contact member 166 includes a flange portion 167 protruding from an outer surface of insulating contact member 166 in a radially outer direction. A holding member 169 is inserted between the insulating contact member 166 and the outer tube 144. The holding member 169 places the insulating contact member 166 inside the outer tube 144, by abutting on the outer tube 144 and the flange portion 167.

Figure 2:
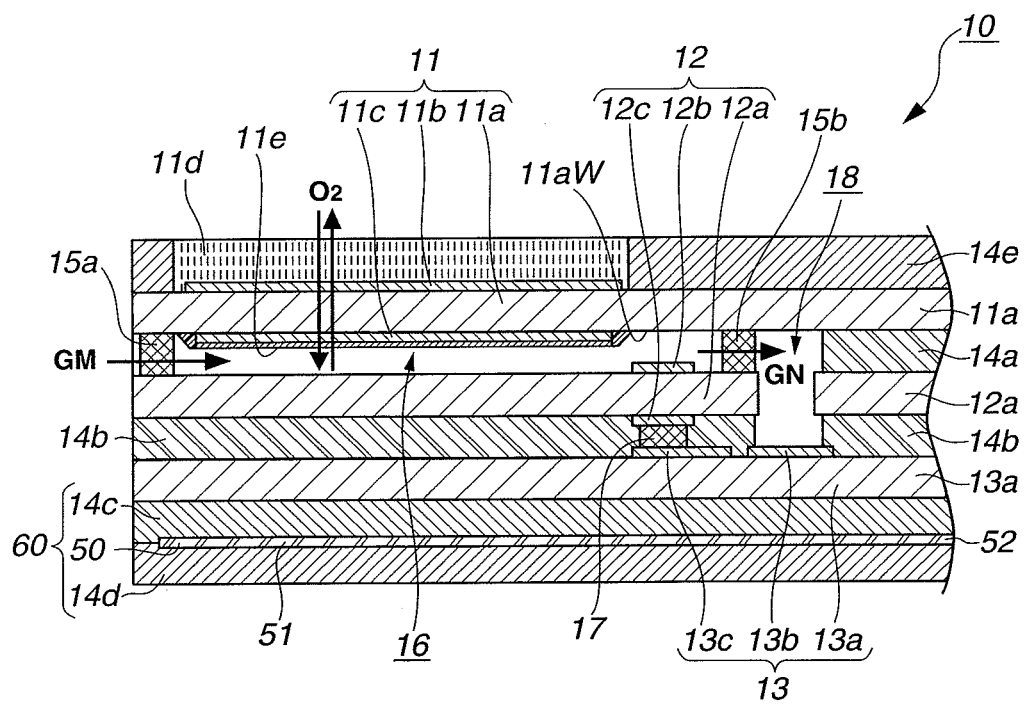
FIG. 2 is a cross sectional view of a NOx sensor element 10.
Figure 2:
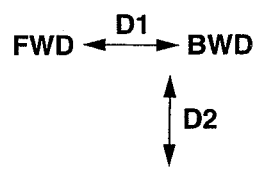

FIG. 2 is a cross sectional view of the NOx sensor element 10. This cross section is parallel to the longitudinal direction D1. The frontward direction (front-end side) FWD is shown by a left direction of FIG. 2, and the backward direction (back-end side) BWD is shown by a right direction of FIG. 2. The NOx sensor element 10 includes an insulating layer 14e, a first solid electrolyte layer 11a, an insulating layer 14a, a third solid electrolyte layer 12a, an insulating layer 14b, a second solid electrolyte layer 13a, and insulating layers 14c and 14d which are laminated in this order. These layers are laminated along a laminating direction D2 perpendicular to the longitudinal direction D1.

A first detection chamber 16 is formed between the first solid electrolyte layer 11a and the third solid electrolyte layer 12a. A detection gas (i.e., gas to be detected) GM is introduced from an external region of the NOx sensor element 10 through a first diffusion resisting member (diffusion control member) 15a into the first detection chamber 16. The first diffusion resisting member 15a is disposed at a left end (inlet) of the first detection chamber 16. A second diffusion resisting member (diffusion control member) 15b is disposed at another end (right end) of first detection chamber 16 which is located opposite to the inlet of first detection chamber 16.

A second detection chamber 18 is formed between the first solid electrolyte layer 11a and the second solid electrolyte layer 13a to pass through the third solid electrolyte layer 12a. The second detection chamber 18 is communicated through the second diffusion resisting member 15*b* with the first detection chamber 16, and is located in the backward direction BWD from the first detection chamber 16.

A heating resistor member 50 extending in the longitudinal direction D1 is buried between the insulating layers 14*c* and 14*d*. The heating resistor member 50 is used for increasing a temperature of gas sensor element 10 up to a predetermined activating temperature and thereby enhancing an oxygen-ion conductivity of each solid electrolyte layer so as to stabilize an operation of gas sensor element 10. The heating resistor member 50 is composed of a heating portion 51 and a heating lead portion 52. The heating portion 51 is formed of an electric conductor such as tungsten, and generates heat by receiving electric power. The heating lead portion 52 transmits an electric power supplied from the after-mentioned lead wires 146, to the heating portion 51. The heating resistor member 50 is supported by the two insulating layers 14*c* and 14*d*. The heating resistor member 50 and the two insulating layers 14*c* and 14*d* constitute a heater 60.

The gas sensor element 10 includes a first oxygen pumping cell 11, an oxygen-concentration sensing cell 12 and a second oxygen pumping cell 13.

The first oxygen pumping cell 11 includes the first solid electrolyte layer 11*a*, an inside first pumping electrode 11*c* (hereinafter, also referred to as "first inner electrode 11*c*"), and a first counter electrode 11*b* (hereinafter, also referred to as "outside first pumping electrode 11*b*") which is a counter electrode to the first inner electrode 11*c*. The inside first pumping electrode 11*c* and the outside first pumping electrode 11*b* are disposed to sandwich the first solid electrolyte layer 11*a* between the inside first pumping electrode 11*c* and the outside first pumping electrode 11*b*. The first inner electrode 11*c* faces the first detection chamber 16. Each of the first inner electrode 11*c* and the outside first pumping electrode 11*b* is mainly formed of platinum. A surface of the first inner electrode 11*c* is coated with a protective layer 11*e* having a porous structure. Moreover, a portion 11*d* of the insulating layer 14*e* which is opposed to (i.e., faces) the outside first pumping electrode 11*b* is formed of a porous body (e.g., alumina) through which gas (e.g., oxygen) can pass.

The oxygen-concentration sensing cell 12 includes the third solid electrolyte layer 12*a*, a sensing electrode 12*b* and a reference electrode 12*c*. The sensing electrode 12*b* and the reference electrode 12*c* are disposed to sandwich the third solid electrolyte layer 12*a* therebetween. The sensing electrode 12*b* faces the first detection chamber 16 in a downstream region beyond the first inner electrode 11*c*, namely faces a portion of first detection chamber 16 which is located downstream from the first inner electrode 11*c*. Each of the sensing electrode 12*b* and the reference electrode 12*c* is mainly formed of platinum.

The insulating layer 14*b* is cut out so that the reference electrode 12*c* abutting on the third solid electrolyte layer 12*a* is placed inside the insulating layer 14*b*. Also, the insulating layer 14*b* is cut out so as to form a reference oxygen chamber 17 inside the insulating layer 14*b*. This reference oxygen chamber 17 is formed by filling the cutout portion of insulating layer 14*b* with a porous body. By applying a constant weak current to the oxygen-concentration sensing cell 12 in advance, oxygen is supplied from the first detection chamber 16 into the reference oxygen chamber 17. Then, an oxygen concentration within the reference oxygen chamber 17 is maintained at a predetermined concentration level. Hence, the reference oxygen chamber 17 is used as a reference for oxygen concentration.

The second oxygen pumping cell 13 includes the second solid electrolyte layer 13*a*, an inside second pumping electrode 13*b* and a second counter electrode 13*c* (hereinafter, also referred to as "counter second pumping electrode 13*c*") which is a counter electrode to the inside second pumping electrode 13*b*. The inside second pumping electrode 13*b* is disposed on a surface of second solid electrolyte layer 13*a* at a portion of second solid electrolyte layer 13*a* which faces the second detection chamber 18. Each of the inside second pumping electrode 13*b* and the counter second pumping electrode 13*c* is mainly formed of platinum. The counter second pumping electrode 13*c* faces the reference oxygen chamber 17, and is disposed on the second solid electrolyte layer 13*a*, namely, abuts on the second solid electrolyte layer 13*a*. The inside second pumping electrode 13*b* faces the second detection chamber 18.

In this embodiment, each of the solid electrolyte layers 11*a*, 12*a* and 13*a* is formed by using zirconia (partially-stabilized zirconia) having oxygen-ion conductivity, as its main component. Each of the insulating layers 14*a* to 14*e* is formed by using alumina as its main component. Each of the first diffusion resisting member 15*a* and the second diffusion resisting member 15*b* is formed by a porous material made of alumina or the like as its main component. It is noted that the "main component" means that a content (contained amount) of that material (mentioned as "main component") in the layer is greater than or equal to 50 wt % of total, for example, the solid electrolyte layer contains zirconia at a rate greater than or equal to 50 wt %. Each of the six layers 14*e*, 11*a*, 12*a*, 13*a*, 14*c* and 14*d* among eight of the solid electrolyte layers and the insulating layers is formed by using a material sheet (e.g., ceramic sheet of zirconia, alumina or the like). Each of the respective electrodes and two insulating layers 14*a* and 14*b* is formed by applying a screen printing to a surface of the ceramic sheet. Then, a laminated body obtained by laminating the pre-burning respective layers is burned, so that the NOx sensor element 10 is formed.

Figure 3:
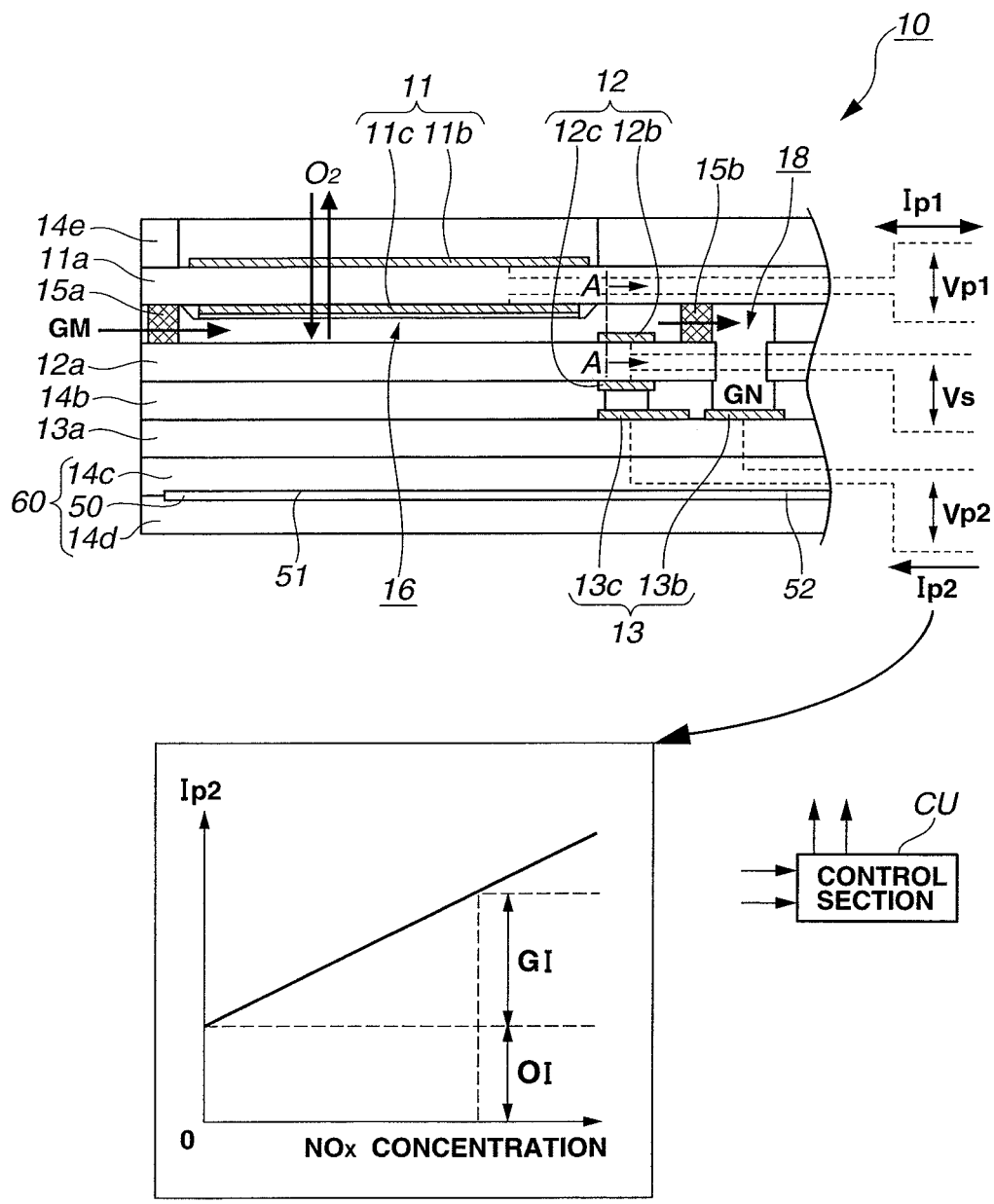
FIG. 3 is an explanatory view showing a control of the NOx sensor element 10.

FIG. 3 is an explanatory view showing a control of the NOx sensor element 10. FIG. 3 shows the NOx sensor element 10 identical with that of FIG. 2. For an easy-to-understand explanation, some signs and hatchings are omitted from FIG. 3. FIG. 3 also shows a control section (control unit) CU of the NOx sensor 200 (the NOx sensor element 10). The control section CU is connected through the connecting terminals 110 and the lead wires 146 shown in FIG. 1 with the heating resistor member 50 and the respective electrodes 11*b*, 11*c*, 12*b*, 12*c*, 13*b* and 13*c* (in this embodiment, some of these electrodes are connected with one common lead wire 146). As mentioned below, the control section CU supplies electric power to the heating resistor member 50. Moreover, the control section CU controls the NOx sensor 200 (the NOx sensor element 10) by sending or receiving signals to or from the respective electrodes 11*b*, 11*c*, 12*b*, 12*c*, 13*b* and 13*c*. In this embodiment, the control section CU is an electronic circuitry constructed by using operational amplifiers and the like. However, instead of this, according to the present invention, the control section CU may be constructed by using a computer including a CPU and a memory.

Next, one example of operation of the NOx sensor element 10 will now be explained. At first, the control section CU is activated by a start of the engine. The control section CU supplies electric power to the heating resistor member 50. The heating resistor member 50 heats the first oxygen pumping cell 11, the oxygen-concentration sensing cell 12 and the second oxygen pumping cell 13, up to their activation temperatures. Then, the control section CU applies an electric current Ip1 to the first oxygen pumping cell 11, in response to a state that each of the cells 11 to 13 has been heated and has reached the activation temperature. Thereby, the first oxygen pumping cell 11 pumps out excessive oxygen included in the detection gas (exhaust gas to be detected) GM which has flowed into the first detection chamber 16, from the first inner electrode 11c toward the first counter electrode 11b.

The control section CU controls an interelectrode voltage (inter-terminal voltage) Vp1 of the first oxygen pumping cell 11 so as to maintain an interelectrode voltage (inter-terminal voltage) Vs of the oxygen-concentration sensing cell 12 at a constant voltage value (e.g., 425 mV). The voltage Vs of oxygen-concentration sensing cell 12 represents an oxygen concentration at a location of the sensing electrode 12b. By this control, the oxygen concentration within the first detection chamber 16 is adjusted to an extent that NOx is slightly decomposed. If oxygen within the first detection chamber 16 becomes short (scarce), oxygen is supplied from the outside first pumping electrode 11b to the first inner electrode 11c. An operation for pumping oxygen out from the first detection chamber 16 and an operation for pumping oxygen into the first detection chamber 16 can be changed to each other by switching a polarity of the interelectrode voltage Vp1 of first oxygen pumping cell 11.

A detection gas (i.e., gas to be detected) GN whose oxygen concentration has been adjusted is introduced through the second diffusion resisting member 15b into the second detection chamber 18. The control section CU applies an interelectrode voltage (inter-terminal voltage) Vp2 to the second oxygen pumping cell 13. This voltage is set at a constant voltage level (a voltage value higher than the control voltage Vs of oxygen-concentration sensing cell 12, for example, 450 mV) which can decompose NOx gas included in the detection gas GN into oxygen gas and nitrogen gas. Thereby, NOx existing in the detection gas GN is decomposed into oxygen and nitrogen.

A second pumping current Ip2 flows through the second oxygen pumping cell 13 so as to pump out an oxygen produced by the decomposition of NOx, from the second detection chamber 18. The second pumping current Ip2 increases approximately in proportion to an amount (concentration) of oxygen generated by the decomposition of NOx. Therefore, the NOx concentration of the detection gas (gas to be detected) GN can be detected by detecting the second pumping current Ip2.

Specifically, in this embodiment, the oxygen concentration inside the first detection chamber 16 is adjusted to a degree capable of decomposing NOx slightly, as mentioned above. That is, the interelectrode voltage Vp1 of first oxygen pumping cell 11 is controlled such that a slight (constant-concentration) oxygen is contained in the detection gas GN which is discharged from the first detection chamber 16. Thus, the detection gas GN contains oxygen having a constant concentration irrespective of the presence or absence of NOx within the detection gas GN. Hence, the second pumping current Ip2 flowing through the second oxygen pumping cell 13 represents a total value of two of an offset (constant value) corresponding to this oxygen concentration and a gain (variable factor) corresponding to the NOx concentration of the detection gas (gas to be detected) GN.

A graph in a lower part of FIG. 3 shows a relation between the second pumping current Ip2 and the NOx concentration of detection gas GM. As shown by the graph, the offset OI takes an approximately constant value irrespective of the NOx concentration, moreover, the gain GI is substantially proportional to the NOx concentration.

It is preferable that the oxygen concentration of detection gas GN is low. Particularly, it is preferable that the oxygen concentration is set to cause a fluctuation range (variation band) of the offset OI to be smaller than 0.1 percent of a variation range (variation band) of the gain GI. In a case that the gas sensor element 10 (particularly, first detection chamber 16) is reduced in size, various advantages can be obtained. For example, a pumping efficiency of the first oxygen pumping cell 11 can be improved, and thereby, a power consumption can be reduced. Moreover, the gas sensor 200 can be downsized. Furthermore, a disparity of temperature within the gas sensor element 10 can be reduced. However, the amount of gas (per unit time) which flows into the gas sensor element 10 (the first detection chamber 16) is reduced due to the downsizing of first detection chamber 16. That is, a gas amount (particularly, amount of NOx) which can be used by the gas sensor element 10 is also reduced. As a result, the variation of gain GI relative to the variation of NOx concentration becomes small. Therefore, it is preferable that the fluctuation (variation) of offset OI is made small, in order to enhance an accuracy when estimating the NOx concentration from the second pumping current Ip2.

There can be various factors (reasons) for the fluctuation of offset OI. The inventors of the present application has discovered a new knowledge that the fluctuation of offset OI can be suppressed by increasing a distance between the first inner electrode 11c and the sensing electrode 12b. This knowledge is found by downsizing the gas sensor element 10 (particularly, first detection chamber 16). This knowledge will now be explained.

Figure 4:
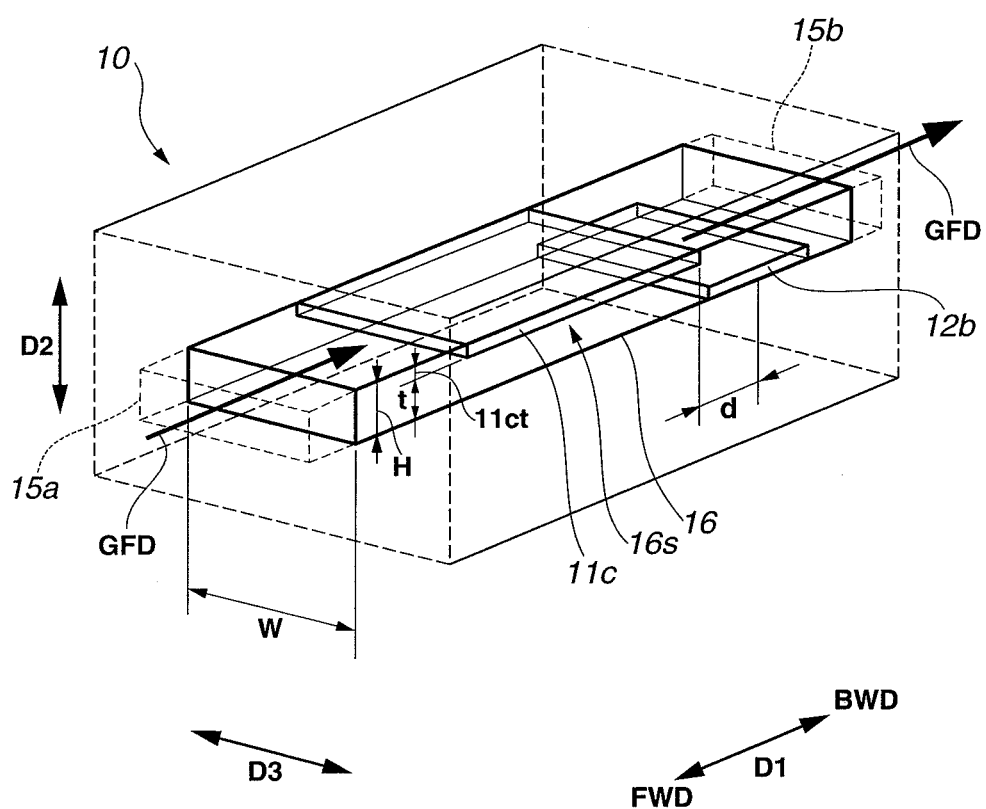
FIG. 4 is an oblique perspective view of a first detection chamber 16.
Figure 5:
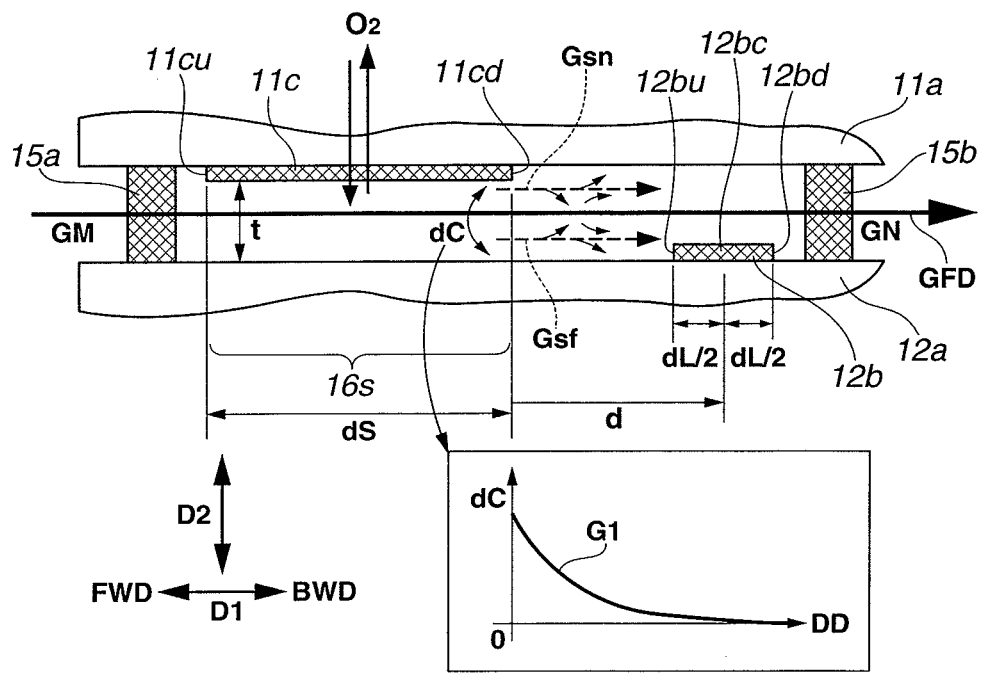
FIG. 5 is a cross sectional view similar as that of FIG. 2.
Figure 6:
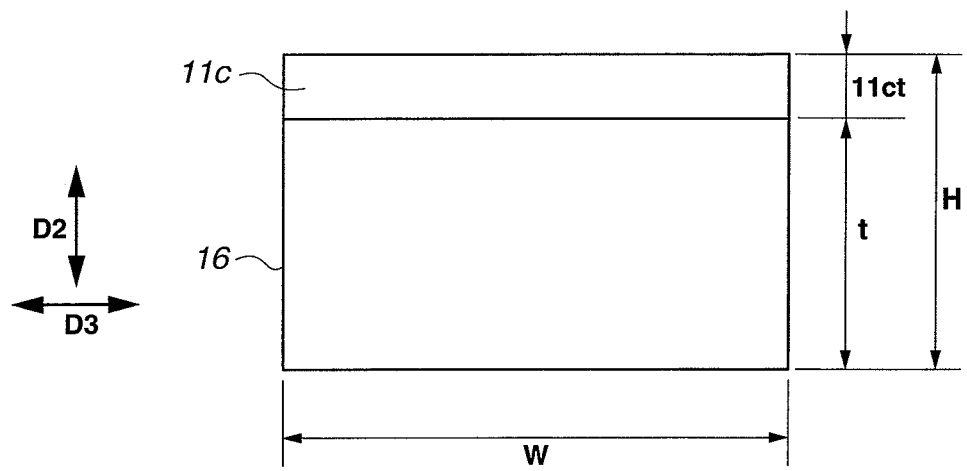
FIG. 6 is a cross sectional view of the first detection chamber 16.

FIG. 4 is an oblique perspective view of the first detection chamber 16. FIGS. 5 and 6 are cross sectional views of the first detection chamber 16. FIG. 4 shows an outer shape of a part of gas sensor element 10 which includes the first detection chamber 16, the first detection chamber 16 located inside the gas sensor element 10, the first inner electrode 11c, the sensing electrode 12b, the first diffusion resisting member 15a, and the second diffusion resisting member 15b (the other components are omitted from the illustration). In FIG. 4, the first detection chamber 16, the first inner electrode 11c and the sensing electrode 12b are shown by thick lines. FIG. 5 is a cross sectional view similar as that of FIG. 2, and shows only a part including the first detection chamber 16. FIG. 6 is a cross sectional view taken by a plane perpendicular to the longitudinal direction D1. This cross section is taken to cut or cross the first inner electrode 11c.

As shown in FIG. 4, in this embodiment, the first detection chamber 16 is a space extending in the longitudinal direction D1, and a shape of this first detection chamber 16 is a substantially rectangular parallelopiped. The detection gas (gas to be detected) flows within the first detection chamber 16 from the frontward side FWD toward the backward side BWD in the longitudinal direction D1. An arrow GFD shown in FIGS. 4 and 5 represents a flow direction of gas (this direction GFD is parallel to the longitudinal direction D1). Thus, the first detection chamber 16 serves also as a gas flow passage extending in the longitudinal direction D1. A cross section (cross section perpendicular to the longitudinal direction D1) of the first detection chamber 16 is a rectangle.

As shown in FIGS. 4 and 5, the first inner electrode 11c is laminated on an upper surface of the first detection chamber 16 (i.e., abuts on a surface of the first solid electrolyte layer 11a). The sensing electrode 12b is laminated on a lower surface of the first detection chamber 16 (i.e., abuts on a surface of the third solid electrolyte layer 12a). This sensing electrode 12b is disposed in a downstream region beyond the first inner electrode 11c.

As shown in FIGS. 4 and 6, a width W of the first detection chamber 16 is taken in a lateral direction (shorter-length direction) D3. The lateral direction D3 is perpendicular to the gas flow direction GFD (=longitudinal direction D1) inside the first detection chamber 16, and also perpendicular to the laminating direction D2 between the first solid electrolyte layer 11a and the first inner electrode 11c. In this embodiment, as viewed in the laminating direction D2, a shape of the first inner electrode 11c is a rectangle extending along the first detection chamber 16 (in the longitudinal direction D1). A width of the first inner electrode 11c is equal to the width W of first detection chamber 16. Similarly as viewed in the laminating direction D2, a shape of the sensing electrode 12b is a rectangle extending along the first detection chamber 16 (in the longitudinal direction D1). A width of the sensing electrode 12b is equal to the width W of first detection chamber 16.

As shown in FIGS. 4 to 6, a sign t represents a height of a space 16s. This space 16s is defined by a part of first detection chamber 16 through which the gas flows and which faces the first inner electrode 11c. That is, this space 16s means a space falling within a position range (explained as follows) relative to the gas flow direction GFD. This position range is defined as a range over which the gas can touch the first inner electrode 11c, and this position range corresponds to a longitudinal length of first inner electrode 11c, as shown in FIG. 5. The height t of the space 16s represents an innermost distance (furthest distance) from the first inner electrode 11c, inside the space 16s. Moreover, the height t is a length obtained by subtracting a thickness 11ct of the first inner electrode 11c from a height H of the first detection chamber 16. Each of the heights H, t and 11ct is a length taken or measured along the laminating direction D2 between the first solid electrolyte layer 11a and the first inner electrode 11c.

FIG. 5 illustrates a graph G1 showing a relation between an oxygen-concentration difference dC and a distance DD. The oxygen-concentration difference dC is a difference of oxygen concentration between a gas Gsn and a gas Gsf. The gas Gsn flows near the first inner electrode 11c (near the surface on which the first inner electrode 11c has been laminated), namely, near the surface of first solid electrolyte layer 11a. The gas Gsf flows away from the first inner electrode 11c. The distance DD represents a distance from a downstream end 11cd of the first inner electrode 11c, in the gas flow direction GFD (longitudinal direction D1).

In the space 16s, the concentration of oxygen included in the gas is adjusted by means of the pumping (pumping-out or pumping-in) of oxygen, through the first inner electrode 11c. Oxygen concentration in a region near the first inner electrode 11c is easy to adjust, as compared with in a region away from the first inner electrode 11c. Accordingly, the difference of oxygen concentration (oxygen-concentration difference dC) can be caused between the region near the first inner electrode 11c (near the surface of first solid electrolyte layer 11a) and the region away from the first inner electrode 11c (away from the surface of first solid electrolyte layer 11a).

The pumping of oxygen is not performed downstream from the downstream end 11cd of first inner electrode 11c. The gas Gsn and the gas Gsf which flow in paths different from each other are gradually diffused and mixed with each other, as these gases Gsn and Gsf proceed in the gas flow direction GFD inside the first detection chamber 16. As a result, the oxygen-concentration difference dC is reduced. Thus, the oxygen-concentration difference dC becomes smaller as the distance DD becomes larger.

A way that the gas Gsn and the gas Gsf which flow in the different paths (different regions) are moved and mixed with each other is influenced by various factors. For example, a temperature of gas sensor 200 can vary according to a variation of flow speed of the exhaust gas flowing in the exhaust pipe or a variation of temperature of the exhaust gas. By such a temperature variation, a temperature difference between the gas Gsn and the gas Gsf might be caused, or this temperature difference between the gas Gsn and the gas Gsf might be varied. By such a temperature difference (variation of temperature difference), the flow of each of gases Gsn and Gsf can be varied. Moreover, in this embodiment, the first solid electrolyte layer 11a (gas Gsn) is far from the heating resistor member 50, and the third solid electrolyte layer 12a (Gsf) is close to the heating resistor member 50, as shown in FIGS. 2 and 3. Accordingly, due to the temperature variation of gas sensor 200, a temperature difference might occur (or vary) between the solid electrolyte layers 11a and 12a, namely, between the gas Gsn and the gas Gsf. Moreover, the flow of each of gases Gsn and Gsf might be varied not only in response to the above-mentioned temperature variation of gas sensor 200 but also in response to various factors (disturbances).

A heater pattern of the heating portion 51 is formed so that a heating center of the heating portion 51 at the time of electric-power supply to the heating resistor member 50 (i.e., a heating portion 51's part which reaches a highest temperature when supplying electric power to the heating resistor member 50) overlaps with the first inner electrode 11c in the gas flow direction GFD (i.e., as viewed in the laminating direction D2).

Therefore, in this embodiment, although the inside second pumping electrode 13b is closer in distance to the heating portion 51 than the first inner electrode 11c, the first inner electrode 11c is closer to the heating center of heating portion 51 than the inside second pumping electrode 13b. Accordingly, during the supply of electric power to the heating portion 51, a temperature in the vicinity of the first inner electrode 11c becomes higher than a temperature in the vicinity of the inside second pumping electrode 13b. Thereby, the temperature of first inner electrode 11c is made high, while maintaining the temperature of inside second pumping electrode 13b in a temperature range incapable of causing a dissociation of $H_2O$. Therefore, in this embodiment, a reduction of measurement accuracy of the detection gas (gas to be detected) can be avoided while improving a pumping ability of oxygen.

Assuming that the sensing electrode 12b is disposed at a location at which the oxygen-concentration difference dC is relatively large (namely, at a location near the first inner electrode 11c), the oxygen concentration of gas which touches or contacts the sensing electrode 12b varies according to the variation of flow of each gas Gsn or Gsf. In this assumption, since the interelectrode voltage Vs (see FIG. 3) is varied according to this variation of oxygen concentration, a feedback control for the pumping which is performed through the first inner electrode 11c is corrected. As a result, the oxygen concentration of detection gas (gas to be detected) GN discharged from the first detection chamber 16 is varied. Such a variation of oxygen concentration of detection gas GN can occur even if a composition of the detection gas GM which flows into the first detection chamber 16 does not vary. In this case, the offset OI (see FIG. 3) is varied in response to the variation of oxygen concentration of detection gas GN. This variation of offset OI results in a measurement error of NOx concentration. Thus, there is a possibility that the detection accuracy of NOx concentration is reduced due to the variation (error) of interelectrode voltage Vs.

Figure 7:
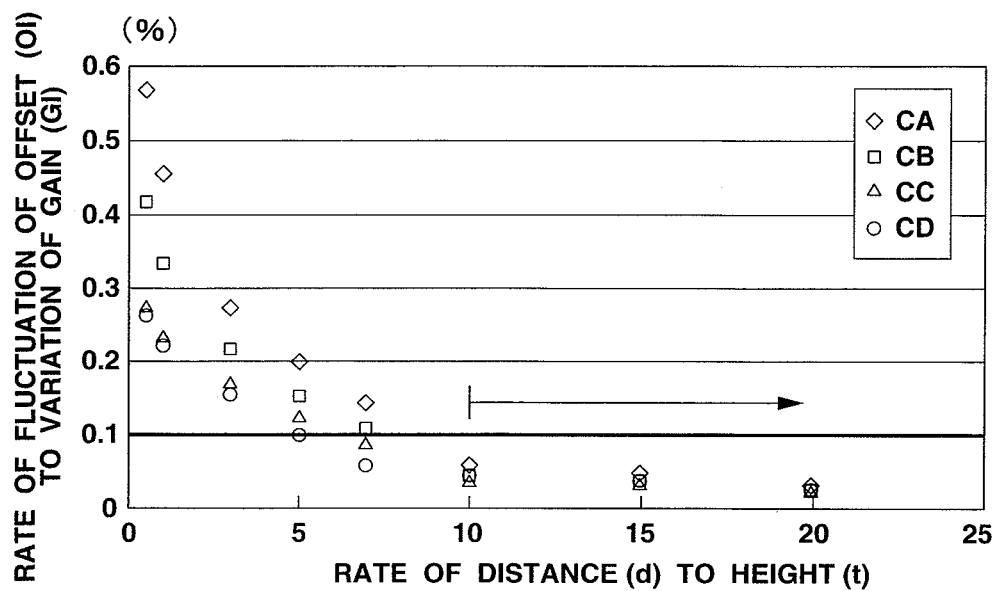
FIG. 7 is a graph showing a relation between a rate of distance d and a rate of fluctuation of offset OI.
Figure 8:
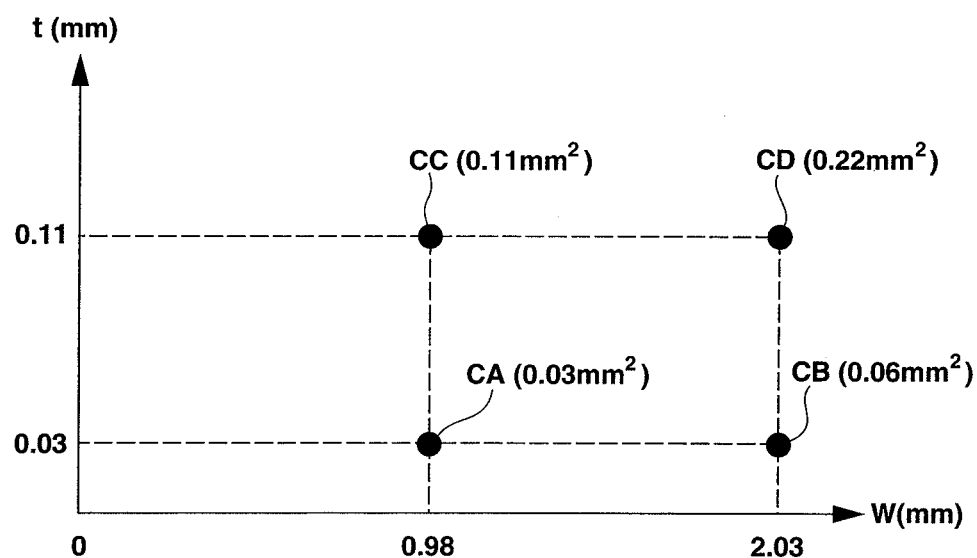
FIG. 8 is an explanatory view showing cross-section sizes.

Therefore, in this embodiment, the sensing electrode 12b is disposed at a location at which the oxygen-concentration difference dC is relatively small (namely, at a location away from the first inner electrode 11c). FIG. 7 is a graph showing a relation between a rate (a distance d/the height t) and the rate of fluctuation (variation) of offset OI. The graph of FIG. 7 shows four kinds of measurement results CA to CD. Between these four kinds of measurement results CA to CD, a cross-section size of the first detection chamber 16 is different. FIG. 8 is an explanatory view showing the cross-section sizes of the respective measurement results CA to CD. A lateral axis of FIG. 8 represents the width W, and a vertical axis of FIG. 8 represents the height t (see FIG. 6). A relation between the measurement results and the sizes is as follows.

The first result CA: the width W is equal to 0.98 mm, the height t is equal to 0.03 mm, and an area (square measure) is equal to 0.03 mm$^2$.

The second result CB: the width W is equal to 2.03 mm, the height t is equal to 0.03 mm, and the area is equal to 0.06 mm$^2$.

The third result CC: the width W is equal to 0.98 mm, the height t is equal to 0.11 mm, and the area is equal to 0.11 mm$^2$.

The fourth result CD: the width W is equal to 2.03 mm, the height t is equal to 0.11 mm, and the area is equal to 0.22 mm$^2$.

Each area (square measure) is a value obtainable by rounding off an original area value to two decimal places. The thickness 11$ct$ (see FIG. 6) of first inner electrode 11$c$ is common (0.01 mm in this embodiment) between the measurement results CA to CD. Moreover, a thickness of sensing electrode 12$b$ (see FIG. 5) is equal to the thickness 11$ct$ of first inner electrode 11$c$.

The four cross-section sizes shown in FIG. 8 have been adopted by the inventors of the present application, as a guide (rough idea) for the cross-section size of a downsized first detection chamber 16. As the cross-sectional area of first detection chamber 16 becomes smaller, the pumping (pumping-out and pumping-in) of oxygen by the first oxygen pumping cell 11 becomes easier and also a temperature difference between components included in the gas sensor element 10 is more suppressed. However, in a case that the cross-sectional area of first detection chamber 16 is excessively small, it is difficult to form the first detection chamber 16. Therefore, it is preferable that the cross-sectional area of the space 16$s$ (see FIGS. 4 and 5) falls within a range (0.03 mm$^2$~0.22 mm$^2$) shown by FIG. 8. That is, if the cross-sectional area is determined by calculation, it is preferable that a value obtained by rounding off an original cross-sectional area value to two decimal places falls within the range from 0.03 mm$^2$ to 0.22 mm$^2$.

Moreover, in a case that the height t (see FIG. 6) of space 16$s$ (see FIGS. 4 and 5) is small, a strength of the gas sensor element 10 can be enhanced. However, in a case that the height t is excessively small, it is difficult to form the first detection chamber 16. Therefore, it is preferable that the height t falls within a range (0.03 mm~0.11 mm) shown by FIG. 8.

Moreover, in a case that the width W (see FIG. 6) of space 16$s$ (see FIGS. 4 and 5) is small, the electrodes 11$c$ and 12$b$ are also small, so that the power consumption can be reduced. However, in a case that the width W is excessively small; the height t has to be excessively large in order to maintain the cross-sectional area, and thereby it is easy to cause (or vary) the temperature difference between the solid electrolyte layers 11$a$ and 12$a$, namely between the gas Gsn and the gas Gsf. Therefore, it is preferable that the width W falls within a range (0.98 mm~2.03 mm) shown by FIG. 8.

It is preferable that the width of sensing electrode 12$b$ is wide. It is more preferable that the width of sensing electrode 12$b$ is equal to the width W of first detection chamber 16. By broadening the width of sensing electrode 12$b$, it can be suppressed that an oxygen-concentration difference within the gas in the width direction affects the interelectrode voltage Vs. Thus, the influence of width W can be reduced as compared with the influence of height t, relative to the distance d which is set in order to obtain a desirable accuracy.

Next, the graph of FIG. 7 will now be explained. As shown in FIG. 5, the distance d represents a distance from the downstream end 11$cd$ of first inner electrode 11$c$ to a center 12$bc$ of the sensing electrode 12$b$ along the gas flow. That is, in this embodiment, the distance d is taken or measured in the gas flow direction GFD (longitudinal direction D1). In detail, the distance d means a length between the downstream end 11$cd$ and the center 12$bc$ of sensing electrode 12$b$ along the gas flow direction GFD, as viewed in the laminating direction D2 of the first solid electrolyte layer 11$a$ and the first inner electrode 11$c$. The center 12$bc$ represents the location of a center point (midpoint) between an upstream end 12$bu$ and a downstream end 12$bd$ of the sensing electrode 12$b$ (namely, represents a location having an equivalent distance (dL/2) from both of the ends 12$bu$ and 12$bd$). In this embodiment, a distance dL between the upstream end 12$bu$ and the downstream end 12$bd$ is equal to 1.2 mm.

In this embodiment, a length of first inner electrode 11$c$ in the gas flow direction GFD, namely a distance dS of the space 16$s$ in the gas flow direction GFD is equal to 4.4 mm. Since a relation of 0.05≦dL/dS≦1.20 is satisfied, a reduction of responsiveness can be avoided while avoiding a reduction of detection accuracy.

Moreover, as is clear from FIG. 5, the downstream end 12$bd$ of sensing electrode 12$b$ is located on the frontward side beyond the second diffusion resisting member 15$b$. Accordingly, in this embodiment, the sensing electrode 12$b$ is less likely to receive the concentration of detection gas of second detection chamber 18 so that the detection accuracy is improved.

In FIG. 7, a rate of the distance d to the height t of space 16$s$ (see FIG. 6) is shown as a lateral axis of FIG. 7. For example, in the case of first result CA (height t: 0.03 mm), the distance d is obtained by a calculation of "0.03×10=0.3 mm" when the lateral axis takes a value equal to 10. Moreover, in the case of third result CC (height t: 0.11 mm), the distance d is obtained by a calculation of "0.11×10=1.1 mm" when the lateral axis takes the value equal to 10.

Figure 9:
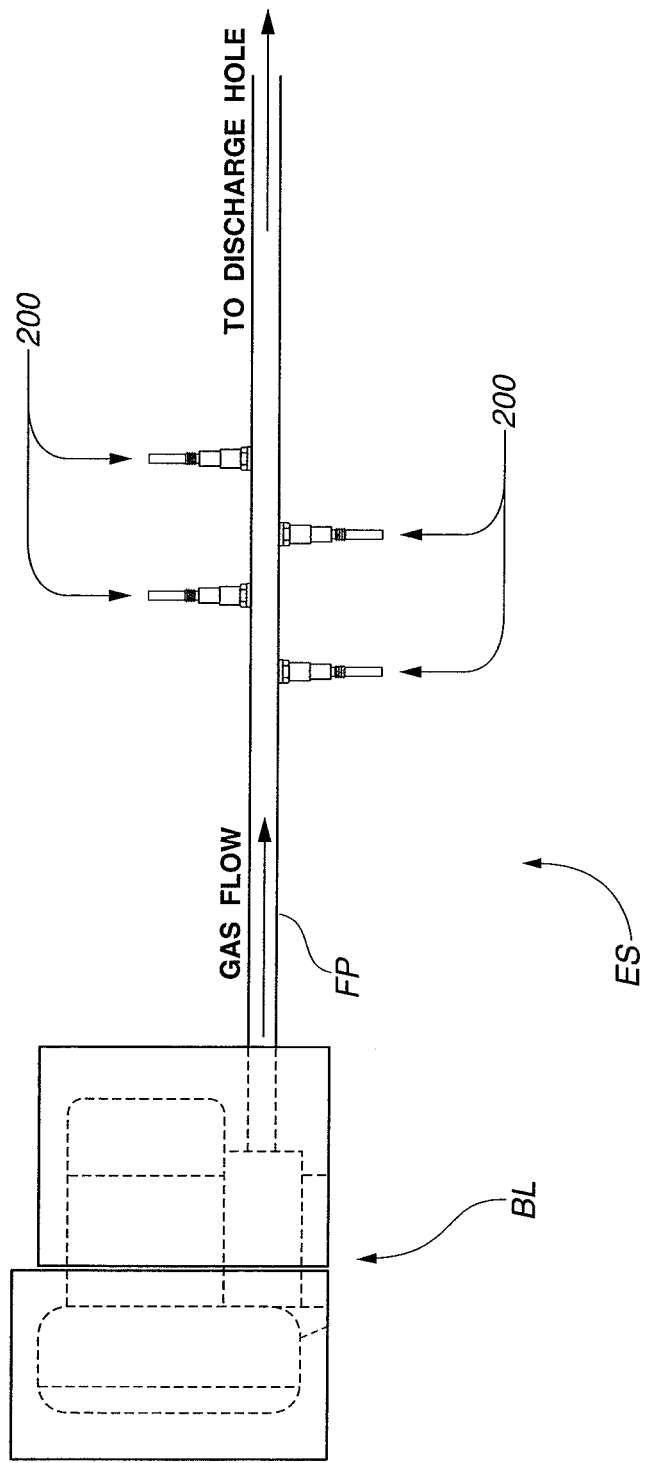
FIG. 9 is an explanatory view of an evaluation system ES.

Next, the fluctuation rate (vertical axis of FIG. 7) of the offset OI will now be explained. FIG. 9 shows an evaluation system ES used in order to obtain the measurement results of FIG. 7. This evaluation system ES includes an air blower BL, a gas flow passage FP connected with the air blower BL, and the gas sensors 200 fixed to the gas flow passage FP. As the air blower BL, a blower having a maximum capability of 3 m$^3$/minute has been employed.

A method for calculating the fluctuation rate of offset OI (i.e., a rate of the fluctuation range of offset OI relative to the variation range of gain GI) is as follows. The evaluation system ES is disposed in an atmosphere at room temperature (approximately from 20 degrees centigrade to 30 degrees centigrade). A control temperature of the NOx sensor element is approximately equal to 700 degrees centigrade. The gas sensor 200 is normally controlled as explained by FIG. 3. Under this condition, a speed of gas flow (air flow) of the air blower BL which is achieved inside the gas flow passage FP is set at 0 m/second. Then, the offset OI under this state is measured and is referred to as "first offset". Next, the speed of gas flow is set at 30 m/sec. Then, the offset OI under this state is measured and is referred to as "second offset". A difference between these first and second offsets is divided by the variation range of gain GI, so that the fluctuation rate of offset OI is calculated (unit: %). It is noted that a value of gain GI corresponding to a practical maximum concentration (approximately 1000 ppm) of NOx is adopted as the variation range of gain GI in this method. Moreover, since the NOx concentration of the gas (air) supplied from the air blower BL in the atmosphere is approximately equal to 0, the measured second pumping current Ip2 represents the offset OI (see FIG. 3). Moreover, each of the offset OI and the gain GI can be change in dependence upon the cross-sectional area of first detection chamber 16.

As shown in FIG. 7, the fluctuation rate of offset OI becomes smaller as the distance d becomes large. This tendency is same as a tendency of the graph G1 of FIG. 5. In all cases of the four kinds of measurement results CA to CD, the fluctuation rate of offset OI is lower than 0.1% when the distance d is greater than or equal to ten times magnitude of the height t. Therefore, by setting the distance d at a value greater than or equal to ten times magnitude of the height t, the fluctuation rate of offset OI can be lowered to reduce the error in NOx detection. In addition, it is estimated that the oxygen-concentration difference dC (see FIG. 5) is small in a case that the height t is small. Hence, it is estimated that this is the reason why the fluctuation rate of offset OI becomes small even when the distance d is small (ten times magnitude of the height t) in the case that the height t is small. Thus, by adjusting the distance d on the basis of the height t, a favorable accuracy can be obtained (see FIG. 7). Moreover, it is preferable that the distance d is smaller than or equal to twenty times magnitude of the height t in order to prevent the size of gas sensor element 10 from becoming excessively large in the longitudinal direction D1 (In the graph of FIG. 7, the fluctuation rate of offset OI is smaller than 0.1% even if the distance d is set at the twenty times magnitude of the height t).

As to a positional relation among the heating portion 51, the first inner electrode 11c and the inside second pumping electrode 13b in the gas flow direction GFD; the heating portion 51 is formed to reach the upstream end 11cu of first inner electrode 11c and a downstream end of the inside second pumping electrode 13b. In other words, the heating portion 51 exists over a gas-flow-directional entire region between the upstream end 11cu of first inner electrode 11c and the downstream end of inside second pumping electrode 13b, as viewed in the laminating direction D2. That is, there is no portion where the heating portion 51 does not exist between the upstream end 11cu and the downstream end of inside second pumping electrode 13b, as viewed in the laminating direction D2. In this embodiment having such a structure, the entire first oxygen pumping cell 11 existing in a range from the upstream end 11cu of first inner electrode 11c to the downstream end of inside second pumping electrode 13b (i.e., the whole from an upstream end of first oxygen pumping cell 11 to a downstream end of first oxygen pumping cell 11) is reliably warmed up by the heating portion 51. Hence, an active state of the first oxygen pumping cell 11 is certainly maintained.

Moreover, a backward (downstream) end of heating portion 51 in the gas flow direction GFD exists at a location frontward (upstream) from an axially front end of the holding portion 160 for holding the NOx sensor element 10. In this embodiment having such a structure, heats of the first oxygen pumping cell 11, the second oxygen pumping cell 13 and the oxygen-concentration sensing cell 12 are prevented from escaping through the holding portion 160. Accordingly, the gas sensor element 10 causes difficulty in being affected in heat by the holding portion 160, so that a stable control of gas sensor is possible in this embodiment.

(B) Modified Embodiments

It is noted that structures except for the structural components claimed in independent Claim(s) among structures explained in the above embodiment are additional components and can be appropriately omitted when carrying out the invention. Moreover, although the invention has been described above with reference to certain embodiment of the invention, the invention is not limited to the embodiment described above. Modifications and variations of the embodiment will occur to those skilled in the art in light of the above teachings. For example, the following modifications are possible.

First Modified Embodiment

In the above-explained embodiment, the gas sensor 200 and the NOx sensor element 10 have the structures as shown in FIGS. 1 to 6. However, the gas sensor 200 and the NOx sensor element 10 according to the present invention do not necessarily have the structures shown in FIGS. 1 to 6, and may have the other various structures. For example, the first diffusion resisting member 15a may be disposed in the shorter-length direction D3 of the first inner electrode 11c. Moreover, the above-mentioned gas sensor 200 (gas sensor element 10) is not necessarily applied to NOx, and can be used for detecting presence/absence or concentration of various oxides. As such oxides, for example, $CO_2$, $SO_2$ or $H_2O$ can be cited. Moreover, according to the present invention, a plurality of cells may be formed by using a common electrolyte layer (electrolyte body). For example, the electrodes 13b and 13c of second oxygen pumping cell 13 may be formed on the third solid electrolyte layer 12a which is commonly used with the oxygen-concentration sensing cell 12. Generally, the gas sensor may include a first electrolyte portion formed (joined) with an electrode of first oxygen pumping cell, a second electrolyte portion formed (joined) with an electrode of second oxygen pumping cell and a third electrolyte portion formed (joined) with an electrode of oxygen-concentration sensing cell. Moreover, these three electrolyte portions may be formed as independent (separate) electrolyte bodies from one another. Alternatively, any two electrolyte portions may be integrally formed by one electrolyte body. Alternatively, the three electrolyte portions may be integrally formed by one electrolyte body.

Second Modified Embodiment

The sizes of respective members included in the gas sensor 200 according to the present invention are not limited to the sizes mentioned in the above embodiment, and may employ the other sizes. For example, the thickness 11ct (see FIG. 6) of first inner electrode 11c may be thicker or thinner than 0.01 mm. Similarly, the thickness of sensing electrode 12b may be thicker or thinner than 0.01 mm. Moreover, the width of sensing electrode 12b may be narrower than the width W of first detection chamber 16. Similarly, the width of first inner electrode 11c may be narrower than the width W of first detection chamber 16. Moreover, the length dL (see FIG. 5) of sensing electrode 12b may be shorter or longer than 1.2 mm if the formula: $0.05 \leq dL/dS \leq 1.20$ is satisfied. Moreover, the length of first inner electrode 11c (i.e., the length from the upstream end 11cu to the downstream end 11cd) has only to be set at a length value sufficient to control the oxygen concentration within first detection chamber 16.

Third Modified Embodiment

Figure 10:
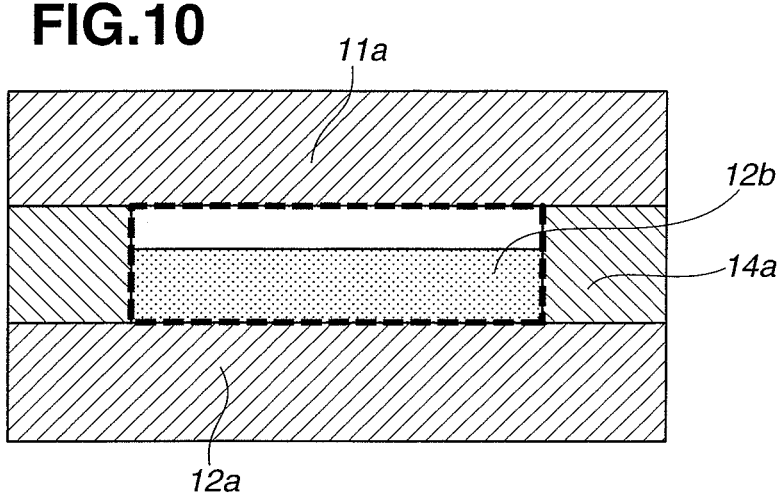
FIG. 10 is one example of a cross-sectional view taken along a line A-A of FIG. 3, in a third modified embodiment.

In the second modified embodiment, it has been mentioned that the thickness and width of sensing electrode 12b may be set at the other sizes. However, it is more preferable that the sensing electrode 12b is formed of porous body, and the sensing electrode 12b includes a portion accounting for greater than or equal to half of the total area of a second cross section of the first detection chamber 16, as viewed in the second cross section. This second cross section is taken perpendicularly to the longitudinal direction D1 at a gas-flow-directional point at which the sensing electrode 12b exists. That is, it is more preferable that the thickness h of sensing electrode 12b is designed to satisfy a relation: W×H≦2×W×h, namely, to satisfy a relation: H≦2h, as shown in FIG. 10. This FIG. 10 is one example of a cross sectional view of sensing electrode 12b, taken along a line A-A of FIG. 3.

Figure 11:
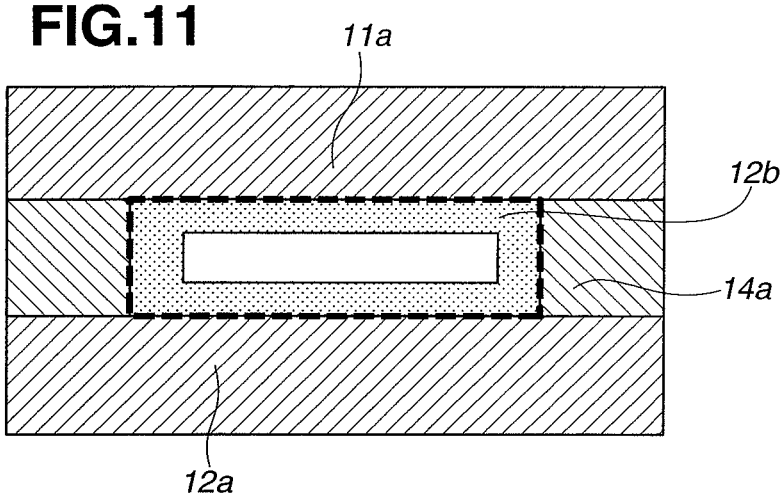
FIG. 11 is another example of the cross-sectional view taken along the line A-A of FIG. 3, in the third modified embodiment.

Moreover, in the case that the sensing electrode 12b is formed of porous body, and the sensing electrode 12b includes its portion accounting for greater than or equal to half of total area of the second cross section of first detection chamber 16, the sensing electrode 12b may be formed to entirely cover a peripheral region (i.e., to be fitted into entire outer-circumference) of the second cross section, as shown in FIG. 11. This FIG. 11 is another example of the cross sectional view of sensing electrode 12b, taken along the line A-A of FIG. 3.

Figure 12:
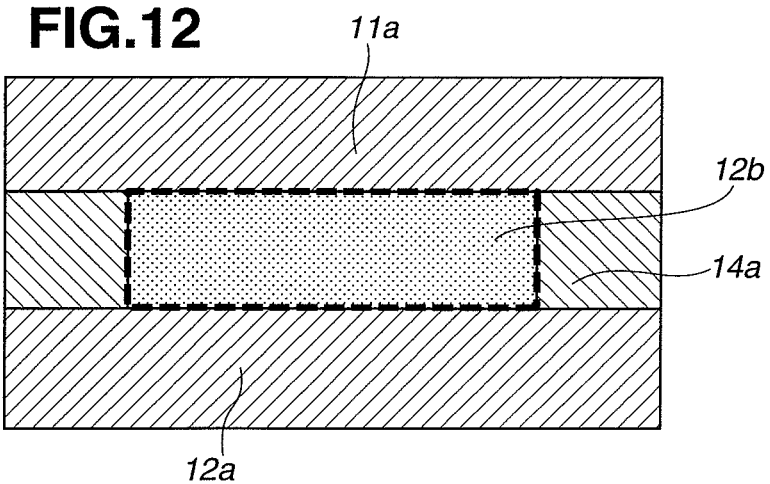
FIG. 12 is still another example of the cross-sectional view taken along the line A-A of FIG. 3, in the third modified embodiment.

It is furthermore preferable that the sensing electrode 12b is formed of porous body, and the sensing electrode 12b is formed to allow its cross-sectional area taken perpendicular to the longitudinal direction D1 to be equal to total area of the second cross section as shown in FIG. 12. This FIG. 12 is still another example of the cross sectional view of sensing electrode 12b, taken along the line A-A of FIG. 3.

Fourth Modified Embodiment

Electrically-conductive material for the electrodes according to the present application is not limited to platinum mentioned in the above embodiment, and may be the other electrically-conductive material(s). For example, gold or silver may be employed as the electrically-conductive material for electrodes according to the present application. Also, materials for the other components of gas sensor 200 according to the present invention are not limited to the materials mentioned in the above embodiment, and various materials can be employed instead.

Fifth Modified Embodiment

The gas sensor (gas sensor element) according to the present invention is not limited to the NOx sensor shown in FIG. 2 in the above embodiment, and each of the other various sensors (elements) can be employed as the gas sensor (gas sensor element) according to the present invention. For example, an air-fuel ratio sensor (oxygen sensor) including a first oxygen pumping cell and an oxygen-concentration sensing cell may be employed as the gas sensor according to the present invention. A structure of such an air-fuel ratio sensor can be attained by omitting the second detection chamber 18 and the second oxygen pumping cell 13 from the gas sensor element 10 shown in FIG. 2.

Next, some advantageous effects according to the above-described embodiment and modified embodiments will now be explained.

(1) According to the above-described embodiments; the gas sensor 200 includes the gas sensor element 10. This gas sensor element 10 includes the first detection chamber 16 into which the gas to be detected is introduced through the first diffusion resisting portion 15a; the first oxygen pumping cell 11 including the first solid electrolyte body 11a and the pair of first electrodes 11b and 11c formed on the first solid electrolyte body 11a; the second detection chamber 18 into which the gas given the oxygen pumping in the first detection chamber 16 is introduced through the second diffusion resisting portion 15b; the second oxygen pumping cell 13 including the second solid electrolyte body 13a and the pair of second electrodes 13b and 13c formed on the second solid electrolyte body 13a; and the oxygen-concentration sensing cell 12 including the third solid electrolyte body 12a and the pair of third electrodes 12b and 12c disposed on the third solid electrolyte body 12a. The pair of first electrodes 11b and 11c include the first inner electrode 11c disposed within the first detection chamber 16, and the first oxygen pumping cell 11 is configured to pump oxygen from/into the gas which has been introduced into the first detection chamber 16. The pair of second electrodes 13b and 13c include the inside second pumping electrode 13b disposed within the second detection chamber 18, and the second oxygen pumping cell 13 is configured to pass an electric current according to the concentration of specific gas component within the second detection chamber 18. The pair of third electrodes 12b and 12c include the sensing electrode 12b disposed within the first detection chamber 16, and the oxygen-concentration sensing cell 12 is configured to generate a voltage between the third electrodes 12b and 12c in accordance with the oxygen concentration within the first detection chamber 16. The sensing electrode 12b is disposed downstream beyond the first inner electrode 11c relative to the gas flow direction GFD. The cross-sectional area of the space 16s of first detection chamber 16 which faces the first inner electrode 11c in the laminating direction D2 has a magnitude falling within a range from 0.03 mm$^2$ to 0.22 mm$^2$. The center of sensing electrode 12b is located downstream beyond the downstream end 11cd of first inner electrode 11c to cause the distance d between the center of sensing electrode 12b and the downstream end 11cd to be greater than or equal to ten times magnitude of the height t of the space 16s of first detection chamber 16, wherein the height t is a length of the space 16s taken in the laminating direction D2.

Since the space 16s which is included in the first detection chamber 16 and which faces the first inner electrode 11c is designed to have a cross-sectional area ranging from 0.03 mm$^2$ to 0.22 mm$^2$, the oxygen-pumping efficiency of oxygen pumping cell can be enhanced, and thereby, the power consumption which is used for the pumping can be reduced. Moreover, the temperature difference between different points in the gas sensor element 10 can be reduced. It is noted that, in a case that the cross-sectional area is smaller than 0.03 mm$^2$, there is a possibility that the first detection chamber 16 becomes difficult to form so that the gas sensor 200 does not perform its function. On the other hand, in a case that the cross-sectional area is greater than 0.22 mm$^2$, the downsizing of the first detection chamber 16 cannot be achieved so that the above-mentioned effects cannot be obtained.

Moreover, the center of sensing electrode 12b is located in a downstream region beyond the downstream end 11cd of first inner electrode 11c to cause the distance d between the center of sensing electrode 12b and the downstream end 11cd to be greater than or equal to ten times magnitude of the height t of space 16s of first detection chamber 16. The reason for the detection errors of sensing electrode 12b is, for example, a phenomenon in which a gas flowing near the first inner electrode 11c of first oxygen pumping cell 11 within the first detection chamber 16 has an oxygen concentration different from that of a gas flowing away from the first inner electrode 11c within the first detection chamber 16. This is because the oxygen concentration of gas flowing near the first inner electrode 11c is easy to adjust as compared with the gas flowing away from the first inner electrode 11c, within the space 16s facing the first inner electrode 11c. On the other hand, in a region downstream from the downstream end 11cd of first inner electrode 11c, these gases having oxygen-concentration values different from each other are diffused and mixed with each other so that the difference of oxygen concentration can be reduced. By virtue of providing such a distance d, the oxygen-concentration difference caused inside the gas to be detected is sufficiently relieved before the gas to be detected reaches the sensing electrode 12b. Hence, the detection error of the oxygen-concentration sensing cell 12 can be reduced. As a result, the detection accuracy of gas sensor 200 can be maintained.

(2) According to the above-described embodiments, the height t is set at a value falling within a range from 0.03 mm to 0.11 mm.

By virtue of this structure, the downsizing of detection chamber can be properly attained while maintaining the detection accuracy of gas sensor 200. It is noted that, if the height t is set at a value smaller than 0.03 mm, there is a possibility that the detection chamber is difficult to form. On the other hand, if the height t is set at a value greater than 0.11 mm, the strength of gas sensor element 10 is reduced.

(3) According to the above-described embodiments, the space 16s' width W taken in a direction perpendicular to both of the gas flow direction GFD and the direction of height t is set at a value falling within a range from 0.98 mm to 2.03 mm.

By virtue of this structure, the downsizing of detection chamber can be properly attained while maintaining the detection accuracy of gas sensor 200. It is noted that, if the width W is set at a value smaller than 0.98 mm, there is a possibility that the detection chamber is difficult to form. On the other hand, if the width W is set at a value greater than 2.03 mm, an area of electrode needs to be increased so that a possibility of increasing the power consumption is caused.

(4) According to the above-described embodiments; the sensing electrode 12b is a porous body, and the sensing electrode 12b includes a portion whose cross-sectional area accounts for greater than or equal to half of total area of the second cross section of first detection chamber 16 which is taken perpendicularly to the gas flow direction GFD at a location where the sensing electrode 12b is present, as viewed in the second cross section.

In the gas sensor 200 having such a structure, the gas to be detected which has been introduced into the first detection chamber 16 passes through the second cross section before reaching the inside second pumping electrode 13b disposed within the second detection chamber 18. Since the sensing electrode 12b includes the portion whose cross-sectional area accounts for greater than or equal to half of the total area of the second cross section of first detection chamber 16 as viewed in the second cross section, a half or more than half of the detection gas (gas to be detected) passes through the sensing electrode 12b formed by porous body. Thereby, oxygen included in the detection gas can be sensed by a wide range included in the second cross section. Therefore, in the gas sensor 200 having such a structure, the detection accuracy of oxygen concentration of the detection gas (gas to be detected) can be further improved even if there is somewhat a difference of oxygen concentration within the detection gas between a region near the sensing electrode 12b and a region away from the sensing electrode 12b.

(5) According to the above-described embodiments; the relation: $0.05 \leq dL/dS \leq 1.20$ is satisfied, where dL denotes a length of the sensing electrode 12b in the gas flow direction GFD, and dS denotes a length of the first inner electrode 11c in the gas flow direction GFD.

By virtue of this structure, the reduction of responsiveness can be prevented while preventing the reduction of detection accuracy. It is noted that, if a relation: $dL/dS < 0.05$ is satisfied, the length of sensing electrode 12b in the gas flow direction GFD is extremely short to reduce a contact area between the sensing electrode 12b and the detection gas (gas to be detected). Due to this, there is a possibility that it is difficult to reliably measure the concentration of the detection gas. That is, there is a possibility that the detection accuracy for the gas to be detected is lowered. On the other hand, if a relation: $1.20 < dL/dS$ is satisfied; the length of sensing electrode 12b in the gas flow direction GFD is extremely long, and thereby, a time length necessary for the detection gas to move from the upstream end 12bu of sensing electrode 12b to the downstream end 12bd of sensing electrode 12b is elongated. Due to this, there is possibility that a time length necessary for a concentration value measured at the downstream end 12bd of sensing electrode 12b to become equal to a concentration value measured at the upstream end 12bu of sensing electrode 12b is elongate. In other words, there is a possibility that a time necessary to measure the concentration of gas is elongated, that is, the responsiveness is reduced.

(6) According to the above-described embodiments; the downstream end 12bd of sensing electrode 12b in the gas flow direction GFD is located upstream beyond (at a more upstream location than) the second diffusion resisting portion 15b.

By virtue of this structure, the sensing electrode 12b can sense a concentration of the detection gas without receiving the concentration of gas existing within the second detection chamber 18. Hence, the sensing accuracy is enhanced.

(7) According to the above-described embodiments; the gas sensor element 10 extends in the gas flow direction GFD and includes the heater 60 laminated therein, and the heater 60 includes the heating portion 51 configured to heat the gas sensor element 10. The heating portion 51 exists to reach the upstream end 11cu of first inner electrode 11c and the downstream end of the inside second pumping electrode 13b, relative the gas flow direction GFD.

By virtue of this structure, an entire range of first oxygen pumping cell 11 which is located in between the upstream (frontward) end 11cu of the first inner electrode 11c and the downstream (backward) end of the inside second pumping electrode 13b can be certainly heated. Therefore, it is easy to maintain whole of the first oxygen pumping cell 11 at its activation temperature.

(8) According to the above-described embodiments; the gas sensor element 10 extends in the gas flow direction GFD and includes the heater 60 laminated therein, and the heater 60 includes the heating portion 51 configured to heat the gas sensor element 10. The heating center of the heating portion 51 overlaps with the first inner electrode 11c relative to the gas flow direction GFD.

In a viewpoint of the enhancement of oxygen pumping ability in the first inner electrode 11c, it is preferable that the temperature of gas sensor element 10 is high when measuring the detection gas (gas to be detected). However, when the temperature of gas sensor element 10 becomes higher than or equal to a certain prescribed temperature value; a dissociation in $H_2O$ included in the detection gas is caused on the inside second pumping electrode 13b so that the measurement of NOx is affected. Hence, it is preferable that the temperature of the inside second pumping electrode 13b remains lower than the prescribed temperature value.

In the gas sensor 200 having the structure of (8), the temperature of first inner electrode 11c can be made high while maintaining the temperature of the inside second pumping electrode 13b in a temperature range preventing the dissociation in $H_2O$. Therefore, the reduction of measurement accuracy of the detection gas can be avoided while enhancing the pumping ability of oxygen as mentioned above.

(9) According to the above-described embodiments; the gas sensor element 10 extends in the gas flow direction GFD and includes the heater 60 laminated therein, and the heater 60 includes the heating portion 51 configured to heat the gas sensor element 10. The gas sensor 200 includes the holding portion 160 holding the gas sensor element 10 to radially surround the gas sensor element 10, and the heating portion 51 is located in a frontward region (side) beyond the axially front end of holding portion 160.

By virtue of this structure, the temperature of gas sensor element 10 is less affected by the temperature of the holding portion 160 since the heating portion 51 of gas sensor element 10 exists at a more frontward location than the holding portion 160. Therefore, a more stable control of gas sensor 200 is possible.

The present invention can be carried out in various modes (aspects). For example, the present invention can be realized as a form of gas sensor, as a form of gas sensor system including a gas sensor and a gas-sensor control apparatus, as a form of gas sensing method, or the like.

This application is based on prior Japanese Patent Applications No. 2009-078169 filed on Mar. 27, 2009 and No. 2010-033137 filed on Feb. 18, 2010. The entire contents of these Japanese Patent Applications are hereby incorporated by reference.

The scope of the invention is defined with reference to the following claims.

What is claimed is:

1. A gas sensor comprising a gas sensor element, the gas sensor element comprising:
   a first detection chamber into which a gas to be detected is introduced through a first diffusion resisting portion;
   a first oxygen pumping cell including a first solid electrolyte body and a pair of first electrodes formed on the first solid electrolyte body, wherein the pair of first electrodes include a first inner electrode disposed within the first detection chamber, wherein the first oxygen pumping cell is configured to pump oxygen from/into the gas which has been introduced into the first detection chamber;
   a second detection chamber into which the gas given the oxygen pumping in the first detection chamber is introduced through a second diffusion resisting portion;
   a second oxygen pumping cell including a second solid electrolyte body and a pair of second electrodes formed on the second solid electrolyte body, wherein the pair of second electrodes include an inside second pumping electrode disposed within the second detection chamber, wherein the second oxygen pumping cell is configured to pass an electric current according to a concentration of specific gas component within the second detection chamber; and
   an oxygen-concentration sensing cell including a third solid electrolyte body and a pair of third electrodes disposed on the third solid electrolyte body, wherein the pair of third electrodes include a sensing electrode disposed within the first detection chamber, wherein the oxygen-concentration sensing cell is configured to generate a voltage between the third electrodes in accordance with an oxygen concentration within the first detection chamber;
   wherein the sensing electrode is disposed downstream beyond the first inner electrode relative to a flow direction of the gas,
   wherein a cross-sectional area of a space of the first detection chamber through which the gas flows falls within a range from $0.03 \text{ mm}^2$ to $0.22 \text{ mm}^2$, the space facing the first inner electrode,
   wherein a center of the sensing electrode is located downstream beyond a downstream end of the first inner electrode to cause a distance between the center of the sensing electrode and the downstream end of the first inner electrode to be greater than or equal to ten times magnitude of a height of the space, the height being a length taken in a laminating direction of the first solid electrolyte body,
   wherein a thickness of the first inner electrode in the laminating direction is smaller than the height of the space facing the first inner electrode.

2. The gas sensor as claimed in claim 1, wherein the height is set at a value falling within a range from 0.03 mm to 0.11 mm.

3. The gas sensor as claimed in claim 1, wherein a width of the space is set at a value falling within a range from 0.98 mm to 2.03 mm, the width being taken in a direction perpendicular to both of the flow direction and a direction of the height.

4. The gas sensor as claimed in claim 1, wherein the sensing electrode is a porous body; and the sensing electrode includes a portion accounting for greater than or equal to half of total area of a cross section of the first detection chamber as viewed in the cross section, the cross section being taken perpendicularly to the flow direction at a location at which the sensing electrode is present.

5. The gas sensor as claimed in claim 1, wherein a relation: $0.05 \leq dL/dS \leq 1.20$ is satisfied, wherein dL denotes a length of the sensing electrode in the flow direction, and dS denotes a length of the first inner electrode in the flow direction.

6. The gas sensor as claimed in claim 1, wherein a downstream end of the sensing electrode in the flow direction is located upstream beyond the second diffusion resisting portion.

7. The gas sensor as claimed in claim 1, wherein the gas sensor element extends in the flow direction and includes a heater laminated therein, the heater including a heating portion configured to heat the gas sensor element; and
the heating portion exists to reach an upstream end of the first inner electrode end a downstream end of the inside second pumping electrode relative the flow direction.

8. The gas sensor as claimed in claim 1, wherein the gas sensor element extends in the flow direction and includes a heater laminated therein, the heater including a heating portion configured to heat the gas sensor element; and
a heating center of the heating portion overlaps with the first inner electrode relative to the flow direction.

9. The gas sensor as claimed in claim 1, wherein the gas sensor element extends in the flow direction and includes a heater laminated therein, the heater including a heating portion configured to heat the gas sensor element;
the gas sensor includes a holding portion holding the gas sensor element to radially surround the gas sensor element; and
the heating portion is located in a region frontward beyond an axially front end of the holding portion.

* * * * *